United States Patent [19]

Gimpelson

[11] Patent Number: 5,059,198

[45] Date of Patent: Oct. 22, 1991

[54] GYNECOLOGICAL TENACULUM

[76] Inventor: Richard J. Gimpelson, 1028 Terracerock Cir., Ballwin, Mo. 63011

[21] Appl. No.: 124,354

[22] Filed: Nov. 23, 1987

Related U.S. Application Data

[63] Continuation of Ser. No. 854,017, Apr. 21, 1986, abandoned.

[51] Int. Cl.⁵ .............................................. A61B 17/28
[52] U.S. Cl. ..................................... 606/119; 606/207
[58] Field of Search .................... 128/321, 322, 346; 606/207, 119

[56] References Cited

FOREIGN PATENT DOCUMENTS 1152220  8/1963  Fed. Rep. of Germany ...... 128/322

OTHER PUBLICATIONS

Mueller, *The Surgical Armamentarium* Catalog (1980), pp. 151, 155, 156.

*Primary Examiner*—Michael H. Thaler
*Attorney, Agent, or Firm*—Armstrong, Teasdale, Schlafly, Davis & Dicus

[57] ABSTRACT

A new Tenaculum for gripping the human uterine cervix presses it against an inserted medical instrument such as the sheath of a hysteroscope. The new tenaculum has a pair of movable extension members which branch into two spaced arms each extending into a knob. Each knob has a tooth which projects toward an oppositely facing knob, with the teeth offset to avoid point to point interface. Each knob has a substantially flat surface for engaging the cervix to better distribute the gripping force. The teeth and knobs are integral with their corresponding extension member.

15 Claims, 1 Drawing Sheet

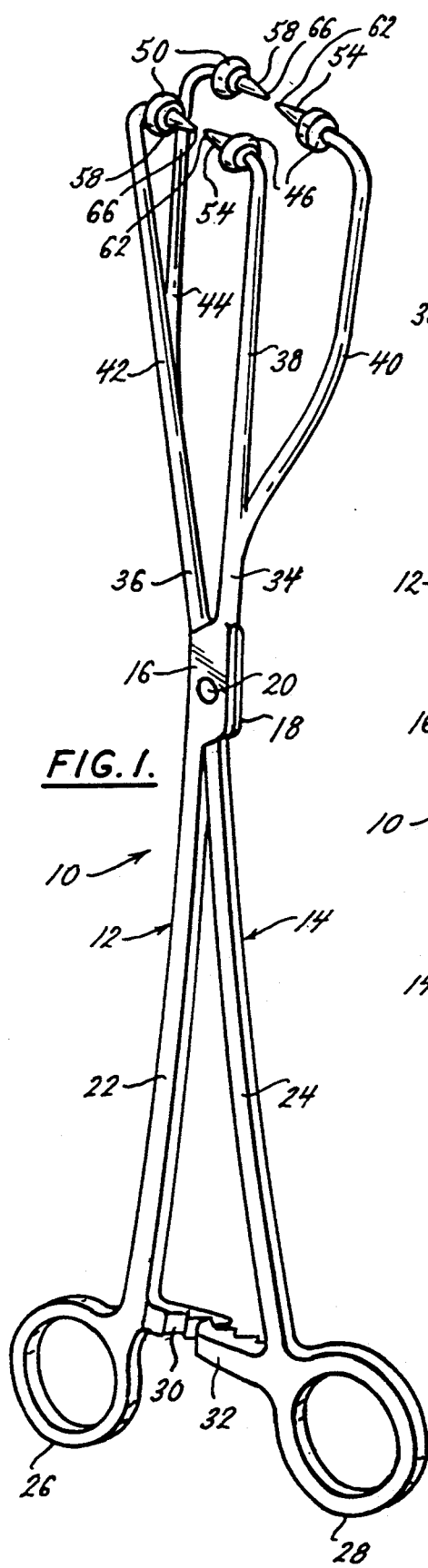
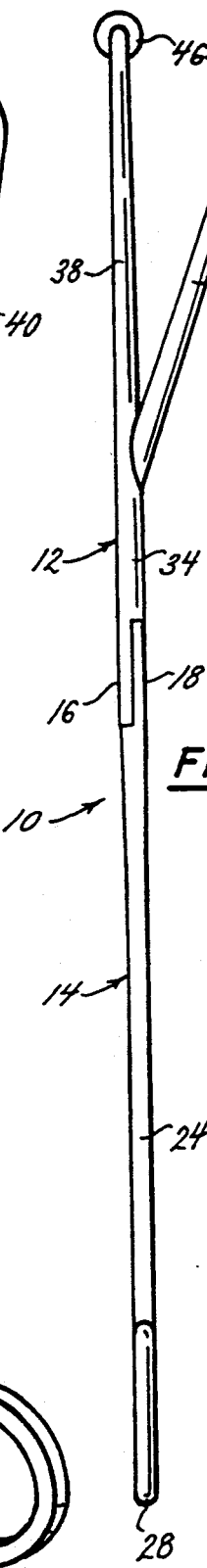
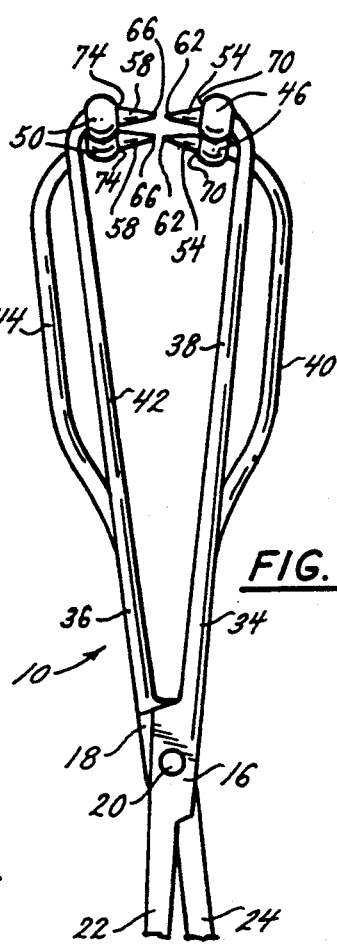
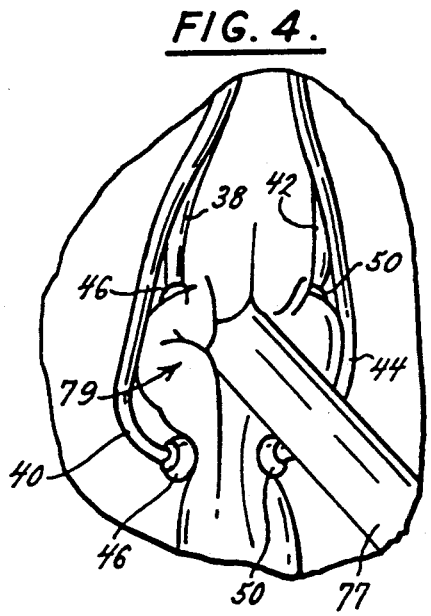

GYNECOLOGICAL TENACULUM

This is a continuation of co-pending application Ser. No. 854,017 filed on 4/21/86 abandoned.

BACKGROUND AND FIELD OF THE INVENTION

The present invention pertains to gynecological tenaculums used for gripping the human female uterine cervix to press the cervix about a medical instrument such as a hysteroscope to prevent the reflux of distension media from the uterus.

Hysteroscopy involves one type of examination of the human uterus. The elongated hysteroscope is used with a surrounding sheath which can have various shapes. The sheath and hysteroscope are inserted through the uterine cervix into the uterus. The space between the sheath and the hysteroscope serves as a conduit for the ingress of a distension medium. The distension medium such as carbon dioxide, a saline solution, Dextran (trademark) 70 liquid solution or Hyskon (trademark) liquid solution, inflates the uterus to permit viewing of the uterine interior for disease, trauma or other problems.

When the uterus is filled with the distension medium, the natural tensile force of the uterine wall can reflux the medium around the sheath's exterior back through the cervix. Refluxing is undesirable in most instances because the uterus must remain inflated for proper examination.

In some instances it is desirable to discharge controlled amounts of distension medium through the cervix to contract the uterus for better examination.

Heretofore, a tenaculum with two pivotally mounted arms having inwardly directed spikes has been used in hysteroscopic examination. The two spikes are placed against the cervix to press it against the sheath. The gripping action is performed solely by the spikes digging into the flesh, and the lack of impedance of such digging causes bleeding, trauma and pain for the patient. It is sometimes necessary to use two of these tenacula, which creates awkwardness and hinders mobility.

Other prior devices have used enlarged tubular members, tubes with enlarged suction sections, and balloons to control refluxing. However these devices do not provide the advantages of the present invention.

The present invention provides advantages over the prior art. The inventive gynecological tenaculum comprises a pair of movably mounted extension members each of which branches into two arms. Each arm has a tooth at its end, and an enlarged section adjacent the tooth.

When a medical instrument such as a hysteroscope and its sheath are inserted through the cervix, the new tenaculum can be conveniently operated by a single hand to cause the four teeth and enlarged sections to grip the cervix and press it against the sheath to stop, or to otherwise control, the reflux of distension media.

The tenaculum places the gripping parts at strategic points for effective pressure distribution of the cervix about the hysteroscope/sheath. The number of gripping parts reduces the pressure needed at any one point of contact to properly grip the cervix. Moreover, the gripping and sealing of the cervix is unaffected by the size and shape of the sheath or enclosure which fits about it. The enlarged sections minimize the penetration of the gripping members into the flesh to thus minimize bleeding and pain. The enlarged sections also provide a surface for engaging the cervix to thus spread the gripping force over a larger part of the tenaculum and reduce the force per square centimeter that is applied to the flesh, to minimize trauma and bleeding. The inventive effects of the enlarged sections are also appreciated with extension members having a single arm.

The inventive tenaculum can be easily and conveniently cleaned and is extremely sanitary. Additionally, it is not necessary to replace parts, such as seals, with the present invention. These features and others are more fully explained in the detailed description that follows.

DESCRIPTION OF THE DRAWINGS

FIG. 1 is an isometric view of the new tenaculum;

FIG. 2 is an end elevation of the new tenaculum;

FIG. 3 is a front view of the upper part of the new tenaculum; and

FIG. 4 shows the sheath for a hysteroscope inserted through the uterine cervix, with the new tenaculum gripping the cervix to press it about the sheath.

DESCRIPTION AND OPERATION OF A PREFERRED EMBODIMENT

The tenaculum 10 comprises a pair of elongated lever members 12 and 14. Intermediate of members 12 and 14 are flat fulcrum bases 16 and 18, respectively, which are pivotally connected by a pivot pin 20.

Beyond the flat bases 16 and 18 the extension members have handles 22 and 24, respectively. Each handle 22 and 24 has a finger or thumb loop 26 and 28, respectively, and an inwardly projecting ratchet bar 30 and 32, respectively.

Above flat bases 16 and 18, the members 22 and 24 extend into a pair of trunks 34 and 36 respectively. Trunk 34 branches into a pair of arms 38 and 40, while trunk 36 branches into a pair of arms 42 and 44. The arms 38, 40, 42, and 44 each bend inwardly near their ends, with arms 38 and 40 extending into knobs 46, and arms 42 and 44 extend into knobs 50. The arms 38 and 42 are substantially straight until they bend into their corresponding knobs, while arms 40 and 44 loop outwardly beyond arms 38 and 42, and then loop back inwardly, as seen clearly in FIG. 3. Knobs 46 and 50 each have integral teeth 54 and 58 of generally conical shape, respectively projecting therefrom. The shapes of the arms 38, 40, 42, and 44 place the teeth 54 opposite teeth 58. The teeth 54 are slightly offset from their corresponding teeth 58 (FIGS. 1 and 3) so that when the teeth are moved together when not gripping anything, the points 62 of teeth 54 and points 66 of teeth 58 contact the sides of the oppositely facing teeth 58 and 54 respectively. This avoids point to point placement against the flesh in use, and minimizes trauma.

The knobs 46 and 50 each have a substantially flat ring 70 and 74, respectively which surround the base of teeth 54 and 58 respectively. Each of the aforesaid members 12 and 14 are one integral piece from its teeth to its handle.

In operation, the tenaculum 10 can be gripped by a single hand so that one of the fingers and the thumb are placed through the loops 26 and 28. Directing attention to FIG. 4, a hysteroscope sheath 77 is shown passing through the canal of a cervix 79 for purposes of examination. The tenaculum 10 can be moved to place the arms 38, 40, 42, and 44 about the cervix 79, and the extension members 12 and 14 then pivoted so that all the teeth 54 and 58, and all the flat knob surfaces 70 and 74 engage the cervix 79 to grip it and press it about the sheath 77 with the desired amount of pressure. In FIG. 4, the arms 40 and 44 extend to allow gripping of the posterior of cervix 79 while the arms 38 and 42 extend to press against the anterior of cervix 79. The outward looping of arms 40 and 44 allows room for the sheath 77 to conveniently fit and be manipulated therebetween.

The surfaces 70 and 74 absorb a considerable part of the compressive force exerted against the cervix 79 and further prevent the penetration of the teeth 54 and 58 into the flesh for any distance greater than the length of the teeth 54 and 58. The tenaculum's pressure can be such to block the reflux of distention medium from the uterus through the cervix 79. If desired the pressure of the tenaculum 10 can be controlled to allow desired amounts of distention media to be refluxed through the canal to facilitate examination. The ratchets 30 and 32 can be interlocked to hold the extension members 12 and 14 in a locked gripping position.

The single handed operation of the tenaculum 10 combined with the four points of pressure allow great mobility and control of the gripping of the cervix 79. The four points of pressure distribution provide for less pressure at each gripping area. During such gripping the hysteroscope/sheath can be slid back and forth through the cervix for examination of different parts of the uterus from a range of distances and perspectives.

The tenaculum 10 can be applied to contact the cervix either before or after insertion of the sheath, or of any other medical instrument. The tenaculum 10 can be used with hysteroscopes and/or sheaths of all sizes and shapes.

There are various changes and modifications which may be made to the invention as would be apparent to those skilled in the art. However, these changes or modifications are included in the teaching of the disclosure, and it is intended that the invention be limited only by the scope of the claims appended hereto.

What is claimed is:

1. A gynecological tenaculum for gripping the exterior of the cervix of the human uterus to press the cervix inwardly against a sheath for a hysteroscope inserted through the cervix canal to resist refluxing of distension media within the uterus through the cervix canal around the sheath, comprising:
   (a) a pair of movable extension members pivotally associated with each other;
   (b) each extension member comprising a trunk and a pair of arms branching distally from each trunk, the length of each arm being greater than the length of the trunk from which it branches;
   (c) the arms having means for gripping the exterior of the cervix to press the cervix inwardly against the sheath to resist the refluxing of distension media through the cervix canal and around the sheath, comprising each arm having an enlarged pressure distribution section near its anterior end, each distribution section having a surface facing inwardly from the distribution section, the surface being positioned for pressing inwardly against the cervix, and a tooth projecting inwardly from each distribution surface for engaging the cervix and pressing the cervix inwardly against the sheath, each pair of arms having an arm that is substantially straight until it reaches a point near the distribution section with said substantially straight arms being in alignment with one another.

2. The gynecological tenaculum of claim 1 wherein the two teeth and two pressure distribution sections of each extension member are spaced from each other a sufficient distance to permit the sheath for the hysteroscope to be inserted therebetween when the teeth and pressure distribution sections grip the cervix and press it inwardly against the sheath.

3. The gynecological tenaculum of claim 1 wherein the length of each tooth is about the same distance as the maximum width of the pressure distribution surface from which it projects.

4. The gynecological tenaculum of claim 1 wherein each tooth has a generally conical shape, and the length of the tooth is about twice the diameter of the base of the tooth.

5. The gynecological tenaculum of claim 1 wherein the enlarged pressure distribution sections are knobs and wherein the pressure distribution surface is a surface of the knob which extends about the base of each tooth.

6. The gynecological tenaculum of claim 5 wherein the pressure distribution surface is substantially flat.

7. A gynecological tenaculum for gripping the exterior of the cervix of the human uterus to press it inwardly against a sheath for a hysteroscope that is inserted through the cervix canal to resist refluxing of distension media within the uterus through the cervix canal around the sheath, comprising:
   (a) a pair of movable extension members pivotally associated with each other;
   (b) each extension member comprising a trunk and a pair of arms branching distally from each trunk, the length of each arm being greater than the length of the trunk from which it branches;
   (c) the arms having means for gripping the exterior of the cervix to press the cervix inwardly against the sheath to resist the refluxing of distension media through the cervix canal, comprising each extension member having near its distal end an integral pressure distribution section comprising a knob, each knob having an inwardly facing pressure distribution surface for engaging the cervix to press the cervix inwardly against the sheath, and each pressure distribution surface having an integral tooth projecting inwardly therefrom so that each tooth can engage the cervix and press it inwardly about the sheath, the teeth being positioned on the pressure distribution surfaces so that when the extension members are pivoted to move the teeth inwardly to the full extent without the cervix therebetween, the teeth will contact each other, and wherein the length of each tooth is not greater than one and one-half times the width of the pressure distribution surface, each pair of arms having an arm that is substantially straight until it reaches a point near the distribution section with said substantially straight arms being in alignment with one another.

8. The gynecological tenaculum of claim 7, wherein each pressure distribution surface is substantially flat and extends completely about the base of each tooth, and wherein teach extension member has a posterior end with an integral loop for receiving the thumb or finger of a hand.

9. A gynecological tenaculum for gripping the exterior of the cervix of the human uterus to press the cervix inwardly against a sheath for a hysteroscope that is inserted through the cervix canal to resist refluxing of distension media within the uterus through the cervix canal around the sheath, comprising:
- (a) a pair of movable extension members pivotally connected to each other by a pivot pin;
- (b) each extension member having a trunk extending distally from the pivot pin, a pair of arms branching distally and integrally from each trunk, the length of each arm being at least one and one-half the length of the trunk from which it branches;
- (c) the arms having means for gripping the exterior of the cervix to press the cervix inwardly against the sheath to resist the refluxing of distension media through the cervix canal comprising each arm having an integral knob with a pressure distribution surface for engaging the exterior of the cervix, a generally conical tooth projecting integrally from each pressure distribution surface for engaging the exterior of the cervix, the pressure distribution surface for each knob extending completely about its respective tooth, the length of each tooth being no more than twice the diameter of the base of the tooth, the teeth and knobs being positioned so that when the extension members are pivoted to move the teeth inwardly, the teeth and the pressure distribution surfaces engage the cervix to press the cervix against the sheath to resist the refluxing of distension media from the uterus through the cervix canal about the sheath, each pair of arms having an arm that is substantially straight until it reaches a point near the integral knob with said substantially straight arms being in alignment with one another.

10. A gynecological tenaculum for gripping the exterior of the cervix of the human uterus to press the cervix inwardly against a sheath for a hysteroscope inserted through the cervix canal, to resist refluxing of distension media within the uterus through the cervix canal around the sheath, comprising:
- (a) a pair of movable extension members pivotally associated with each other;
- (b) each extension member having a trunk and first and second arms branching distally from each trunk, the first arm extending along an axis which is in substantially the same direction as the axis of the trunk, and the second arm being offset relative to the trunk;
- (c) the arms having means for gripping the exterior of the cervix to press the cervix inwardly against the sheath to resist the refluxing of distension media through the cervix canal and around the sheath, comprising each arm having an enlarged pressure distribution section near its anterior end, each distribution section having a surface facing inwardly from the distribution section, the surface being positioned for pressing inwardly against the cervix, and a tooth projecting inwardly from each distribution section for engaging the cervix and pressing the cervix inwardly against the sheath.

11. The gynecological tenaculum of claim 10 wherein the second arm has a part that extends at an angle of at least 20° relative to the axis of the trunk from which it branches.

12. The gynecological tenaculum of claim 10 wherein the enlarged pressure distribution sections are knobs and wherein the pressure distribution surface is a surface of the knob which extends about the base of each tooth.

13. A gynecological tenaculum for gripping the exterior of the cervix of the human uterus to press the cervix inwardly against a sheath for a hysteroscope inserted through the cervix canal to resist refluxing of distension media within the uterus through the cervix canal around the sheath, comprising:
- (a) a pair of movable extension members pivotally connected with each other;
- (b) each extension member comprising a trunk and first and second arms integrally extending from each trunk, the first arm extending along an axis that is in substantially the same direction as the axis of the trunk, and the second arm having a part extending at an angle of at least twenty degrees relative to the axis of the trunk from which it branches, the arms being spaced from each other to permit the hysteroscope to be easily inserted and maneuvered therebetween, the length of each arm being at least one and one-half of the length of the trunk from which it branches, with the first arms branching from each trunk being in alignment with one another, and the second arms branching from each trunk being aligned with one another, and;
- (c) the arms having a tooth projecting inwardly for engaging the cervix and pressing the cervix inwardly against the sheath, each arm having an enlarged knob adjacent the teeth from which each tooth extends, and each knob having a pressure distribution section having a surface being positioned for pressing inwardly against the cervix.

14. A gynecological tenaculum for gripping the exterior of the cervix of the human uterus to press the cervix inwardly against a sheath for a hysteroscope inserted through the cervix canal to resist refluxing of distension media within the uterus through the cervix canal around the sheath, comprising:
- (a) a pair of movable extension members pivotally associated with each other;
- (b) each extension member comprising a trunk and a pair of arms branching distally from each trunk, the length of each arm being greater than the length of the trunk from which it branches;
- (c) the arms having means for gripping the exterior of the cervix to press the cervix inwardly against the sheath to resist the refluxing of distension media through the cervix canal and around the sheath, comprising each arm having an enlarged pressure distribution section near its anterior end, each distribution section having a surface facing inwardly from the distribution section, the surface being positioned for pressing inwardly against the cervix, and a tooth projecting inwardly from each distribution surface for engaging the cervix and pressing the cervix inwardly against the sheath, each pair of arms having an arm that is substantially straight until it reaches a point near the distribution section with said substantially straight arms being in alignment with one another, and wherein the other arms of each extension member are in alignment with each other and each have parts that loop outwardly from their branching points from the trunk and then loop inwardly to provide space between the looping parts for ease of manipulation of the sheath and hysteroscope therebetween, and the arms having the looping parts being separated from each other at their midpoints a distance that is at least one and one-half the distance of separation between the other two arms at their midpoints.

15. The gynecological tenaculum of claim 14 wherein the length of the looping part of each arm is considerably greater than the length of the trunk from which that arm branches.

* * * * *